(12) United States Patent
Simon et al.

(10) Patent No.: US 10,813,604 B2
(45) Date of Patent: Oct. 27, 2020

(54) VOLUMETRIC IMAGING SYSTEM FOR HEALTH SCREENING

(71) Applicant: CARESTREAM HEALTH, INC., Rochester, NY (US)

(72) Inventors: Richard A. Simon, Rochester, NY (US); Nathan J. Packard, Provo, UT (US)

(73) Assignee: Carestream Health, Inc., Rochester, NY (US)

( * ) Notice: Subject to any disclaimer, the term of this patent is extended or adjusted under 35 U.S.C. 154(b) by 48 days.

(21) Appl. No.: 15/779,870

(22) PCT Filed: Dec. 13, 2016

(86) PCT No.: PCT/US2016/066246
§ 371 (c)(1),
(2) Date: May 30, 2018

(87) PCT Pub. No.: WO2017/106113
PCT Pub. Date: Jun. 22, 2017

(65) Prior Publication Data
US 2018/0353145 A1    Dec. 13, 2018

Related U.S. Application Data

(60) Provisional application No. 62/267,427, filed on Dec. 15, 2015.

(51) Int. Cl.
*A61B 6/10* (2006.01)
*A61B 6/00* (2006.01)
(Continued)

(52) U.S. Cl.
CPC .............. *A61B 6/107* (2013.01); *A61B 6/027* (2013.01); *A61B 6/035* (2013.01); *A61B 6/04* (2013.01);
(Continued)

(58) Field of Classification Search
CPC ....... A61B 6/107; A61B 6/027; A61B 6/0407; A61B 6/4435; A61B 6/46; A61B 6/54;
(Continued)

(56) References Cited

U.S. PATENT DOCUMENTS 6,735,274 B1    5/2004   Zahavi et al.
7,003,070 B1    2/2006   Chen et al.
(Continued)

FOREIGN PATENT DOCUMENTS

CN    103300876        9/2013
CN    103300876 B  *  2/2015
(Continued)

OTHER PUBLICATIONS

International Search Report dated Mar. 17, 2017 for International Application No. PCT/US2016/066246, 3 pages.

*Primary Examiner* — Courtney D Thomas

(57) ABSTRACT

An apparatus having an x-ray source and an x-ray detector configured to be rotated about a standing patient to capture and store a plurality of radiographic images of the patient during the rotation. A portable enclosure surrounds the source, the detector and the patient.

20 Claims, 10 Drawing Sheets

(51) Int. Cl.
  *A61B 6/02* (2006.01)
  *A61B 6/04* (2006.01)
  *G21F 5/02* (2006.01)
  *A61B 6/03* (2006.01)
  *G21F 3/00* (2006.01)

(52) U.S. Cl.
  CPC .......... *A61B 6/0407* (2013.01); *A61B 6/4405* (2013.01); *A61B 6/4435* (2013.01); *A61B 6/46* (2013.01); *A61B 6/54* (2013.01); *A61B 6/563* (2013.01); *G21F 5/02* (2013.01); *A61B 6/4007* (2013.01); *A61B 6/488* (2013.01); *G21F 3/00* (2013.01)

(58) Field of Classification Search
  CPC ......... A61B 6/563; A61B 6/4405; A61B 6/04; A61B 6/035; A61B 6/488; A61B 6/4007; G21F 5/02; G21F 3/00
  See application file for complete search history.

(56) References Cited

U.S. PATENT DOCUMENTS

| 7,224,764 | B2* | 5/2007 | Sukovic | A61B 6/032 |
| | | | | 378/19 |
| 2006/0210021 | A1* | 9/2006 | Matsumoto | A61B 6/04 |
| | | | | 378/196 |
| 2010/0177865 | A1* | 7/2010 | Yoshimura | A61B 6/14 |
| | | | | 378/19 |
| 2016/0015336 | A1* | 1/2016 | Ballsieper | A61B 6/107 |
| | | | | 250/515.1 |

FOREIGN PATENT DOCUMENTS

| EP | 1 702 566 | 9/2006 |
| JP | S52-37469 U | 3/1977 |
| JP | 2007-236817 | 9/2007 |
| JP | 2013-111316 | 6/2013 |
| JP | 2015-198724 | 11/2015 |
| KR | 10-2006-0135132 | 12/2006 |
| WO | 2004/003934 | 1/2004 |

* cited by examiner

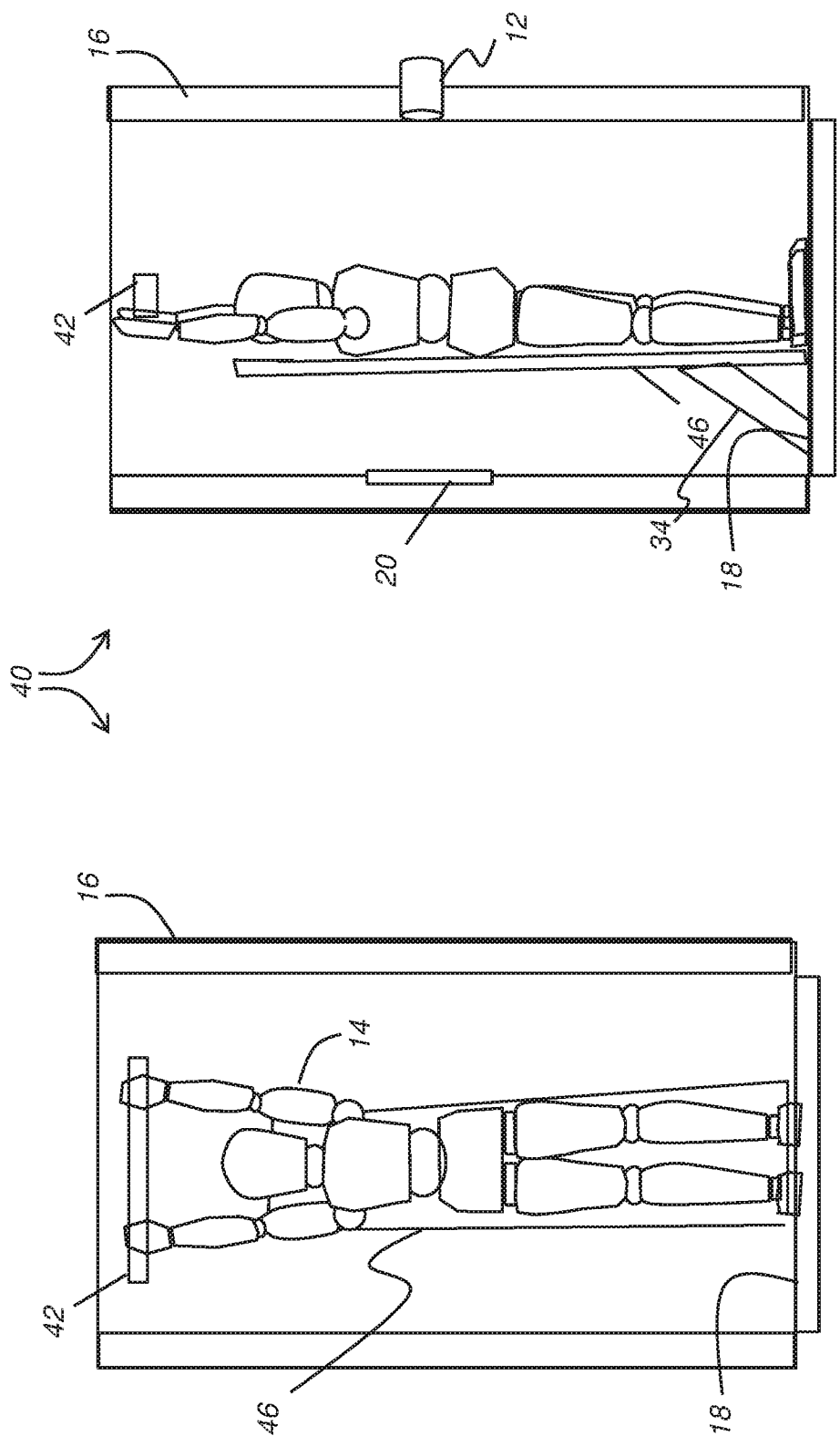

VOLUMETRIC IMAGING SYSTEM FOR HEALTH SCREENING

CROSS REFERENCE TO RELATED APPLICATIONS

This application claims the benefit of and is a U.S. National Phase filing of PCT Application PCT/US2016/066246 filed Dec. 13, 2016 entitled "VOLUMETRIC IMAGING SYSTEM FOR HEALTH SCREENING", in the name of Simon et al., which claims benefit of U.S. Provisional application Ser. No. 62/267,427, provisionally filed on Dec. 15, 2015, entitled "VOLUMETRIC IMAGING SYSTEM FOR LUNG HEALTH SCREENING", in the name of Simon et al., all of which are hereby incorporated by reference herein in their entirety.

BACKGROUND OF THE INVENTION

This disclosure relates generally to the field of radiographic imaging, in particular, to radiographic volume imaging and to apparatuses and methods for acquiring projection images of a patient such as for chest x-ray screenings.

There is a need for a low cost, portable radiographic imaging device that may be used in remote areas for patient-accessible low-dose screening, such as for lung cancer and other conditions. In particular, it would be advantageous to be able to provide the benefits of volume imaging, wherein a three-dimensional (3-D) image of a subject, such as the chest of a patient, may be obtained at any of a broad range of possible remote sites, including in areas not typically provided with radiographic imaging facilities, and without requiring the high overhead of a full-scale radiography facility or the high cost of attending staff for screening functions. In order to allow more widespread use of the benefits of 3-D imaging for screening, design of a volume imaging apparatus is constrained by cost, usability, and dimensional factors, as well as radiation management factors associated with radiographic imaging equipment.

There have been a number of solutions proposed to meet the need for portable volume imaging apparatuses, including those described in U.S. Pat. No. 7,003,070 to Chen et al.; U.S. Pat. No. 6,735,274 to Zahavi et al.; and U.S. Pat. No. 7,224,764 to Sukovic et al. Some drawbacks of proposed solutions include high cost, mechanical complexity, and lack of flexibility for handling different types of screening and for adapting to differences between individuals in the patient population. Proposed solutions do not provide sufficient shielding for stand-alone use of the system outside the confines of a shielded radiographic facility and thus would not be appropriate for broader clinical use or for access outside a fully featured radiography site that is designed with integrated shielding.

Thus, it may be seen that there would be advantages in providing a volume imaging apparatus that would allow more widespread access to high-volume screening in a clinical environment as well as in other environments not typically associated with conventional radiography equipment.

The discussion above is merely provided for general background information and is not intended to be used as an aid in determining the scope of the claimed subject matter.

BRIEF DESCRIPTION OF THE INVENTION

An apparatus having an x-ray source and an x-ray detector is configured to be rotated about a standing patient to capture and store a plurality of radiographic images of the patient during the rotation. A portable enclosure surrounds the source, the detector and the patient. An advantage that may be realized in the practice of some disclosed embodiments of the apparatus is to provide imaging availability at locations remote from standard medical facilities.

In one embodiment, an apparatus includes an x-ray source assembly and a detector assembly configured to rotate about a central axis to capture and store a plurality of radiographic images of a patient positioned at the central axis. An x-ray shielded enclosure is attached to the x-ray source assembly and the x-ray detector assembly, and is configured to entirely enclose the source assembly, the detector assembly and the patient, and is transportable as a unit.

In one embodiment, an x-ray source is positioned on one side of a central axis, an x-ray detector is positioned on a second side of the central axis opposite the x-ray source. The detector is configured to capture and store a plurality of radiographic images of a patient standing at the central axis. A platform is configured to support the patient standing thereon and to rotate the standing patient at the central axis between the source and detector. An x-ray shielded portable enclosure surrounds the source, the detector and the patient.

In one embodiment, an apparatus having a stationary x-ray detector and a movable x-ray source rotates the x-ray source as it moves to continuously aim the source at the detector. The source is configured to emit x-rays at predetermined times during its movement so that the detector captures radiographic images of a patient standing therebetween. An x-ray shielded enclosure attached to the x-ray source and the x-ray detector entirely enclosed the source, the detector and the patient during imaging, and is transportable as a unitary integrated whole.

According to one aspect of the present invention, there is disclosed an apparatus comprising an x-ray source, an x-ray detector, a mechanism attached to the source and the detector to rotate the source and detector about a standing person. The source and detector may be configured to capture and store a plurality of radiographic images of the person while being rotated. An x-ray shielded portable enclosure to enclose the source, the detector, the mechanism, and the standing person.

According to one aspect of the present invention, there is disclosed an apparatus comprising an x-ray source, an x-ray detector, and a platform to support a person standing thereon. The platform may be configured to rotate the standing person between the source and detector while the source and detector capture and store a plurality of radiographic images of the person during rotation. An x-ray shielded portable enclosure surrounds the source, the detector and the standing person.

According to another aspect of the present invention, there is disclosed an apparatus comprising an x-ray source, an x-ray detector, and a mechanism attached to the source which moves the source relative to a person standing between the source and the detector. The detector captures and stores a plurality of radiographic images of the person while the source is moved. An x-ray shielded portable enclosure completely encloses the source, the detector, the mechanism, and the standing person.

An object of the present disclosure is to address the need for improved volume image acquisition apparatus for low dose screening and related projection and volume imaging applications. Embodiments of the present disclosure provide a portable volume imaging apparatus that allows a high-degree of operation and allow patient imaging with minimal or no technician assistance.

These objects are given only by way of illustrative example, and such objects may be exemplary of one or more embodiments of the invention. Other desirable objectives and advantages inherently achieved may occur or become apparent to those skilled in the art. The invention is defined by the appended claims.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention may be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference may be made to the following detailed description, read in connection with the drawings in which:

FIGS. 5A and 5B are schematic diagrams that show different views of exemplary patient support components within an enclosure chamber used for CBCT image acquisition;

DETAILED DESCRIPTION OF THE EMBODIMENTS

Figure 1:
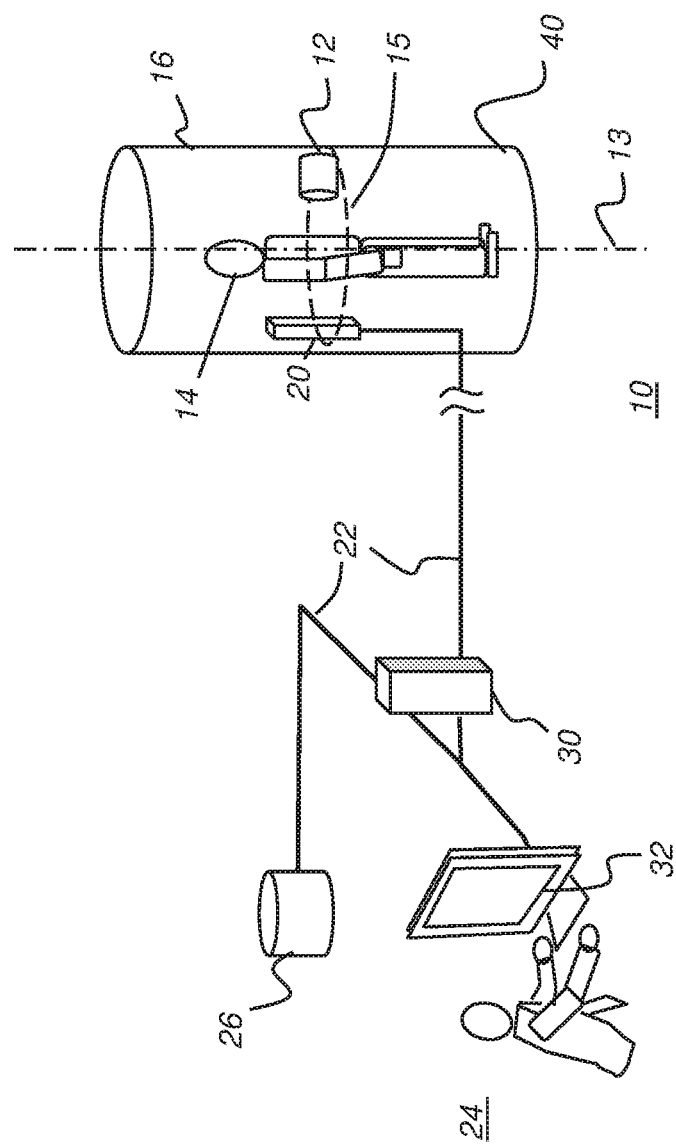
FIG. 1 is a schematic diagram showing components of an exemplary imaging system.

This application claims priority to U.S. Patent Application Ser. No. 62/267,427, filed Dec. 15, 2015, in the name of Simon et al., and entitled VOLUMETRIC IMAGING SYSTEM FOR LUNG HEALTH SCREENING, which is hereby incorporated by reference in its entirety.

The following is a detailed description of the preferred embodiments, reference being made to the drawings in which the same reference numerals identify the same elements of structure in each of the several figures.

Where they are used herein, the terms "first", "second", and so on, do not necessarily denote any ordinal, sequential, or priority relation, but are simply used to more clearly distinguish one element or set of elements from another, unless specified otherwise.

In the context of the present disclosure, the terms "viewer", "operator", "viewing practitioner", "observer", and "user" are considered to be equivalent and refer to the viewing practitioner or other person who views and manipulates an x-ray image on a display monitor or other viewing apparatus.

As used herein, the term "energizable" relates to a device or set of components that perform an indicated function upon receiving power and, optionally, upon receiving an enabling signal.

The term "actuable" has its conventional meaning, relating to a device or component that is capable of effecting an action in response to a stimulus, such as in response to an electrical signal, for example.

The term "modality" is a term of art that refers to types of imaging. Modalities for an imaging system may be conventional x-ray radiography, fluoroscopy or pulsed radiography, tomosynthesis, tomography, ultrasound, magnetic resonance imaging (MRI), or other types of imaging. The term "subject" refers to the patient who is being imaged and, in optical terms, may be considered equivalent to the "object" of the corresponding imaging system.

The term "set", as used herein, refers to a non-empty set, as the concept of a collection of elements or members of a set is widely understood in elementary mathematics. The terms "subset" or "partial subset", unless otherwise explicitly stated, are used herein to refer to a non-empty proper subset, that is, to a subset of the larger set, having one or more members. For a set S, a subset may comprise the complete set S. A "proper subset" of set S, however, is strictly contained in set S and excludes at least one member of set S. A "partition of a set" is a grouping of the set's elements into non-empty subsets so that every element is included in one and only one of the subsets. Two sets are "disjoint" when they have no element in common.

The terms "image" and "image data" may be used interchangeably in the context of the present disclosure. A digital image that is captured by a digital imaging apparatus may be processed, displayed, transmitted, and/or stored as image data.

For the image processing steps described herein, the term "image pixels" is used to refer to image data elements, conventionally used with respect to 2-D imaging and image display, and "voxels" is used for volume image data elements, often used with respect to 3-D imaging, and may be used interchangeably. It should be noted that the 3-D tomosynthesis image may itself be synthesized from 2-D image data obtained as image pixels on a 2-D sensor array and displays as a 2-D image from one angle of view. Thus, 2-D image processing and image analysis techniques may be applied to the 3-D volume image data. In the description that follows, image processing techniques described as operating upon pixels may alternately be described as operating upon the 3-D voxel data that is stored and represented in the form of 2-D pixel data for display. In the same way, techniques that operate upon voxel data may also be described as operating upon pixels.

With respect to an image detector, the term "imaging pixel" refers to a picture element unit cell containing a photosensitive element and related circuitry for converting incident electromagnetic radiation to an electrical signal.

In the context of the present disclosure, "tomographic imaging apparatus" include various types of imaging systems that scan the subject patient to acquire a number of 2-D radiographic projection images using radiant energy that is directed toward the patient from a range of different positions, then process the 2-D projection images to reconstruct a 3-D image of the subject. For the sake of description, the present disclosure primarily discloses a cone-beam computed tomography (CBCT) imaging modality. However, other types of tomographic imaging apparatus may be used, including generalized computed tomography (CT) systems such as those using fan beam radiant energy or tomosynthesis imaging systems that scan over a limited angular range, i.e., less than 360° or less than 180°. These systems may also be individually referred to as a "radiographic volume imaging apparatus" in the present disclosure.

The schematic diagram of FIG. 1 shows an imaging system 10 that may be used to acquire projection images of a subject 14. The projection images may be used for generating volume images of a subject 14 using a cone-beam computed tomography (CBCT) imaging apparatus 40. The imaging apparatus 40 has a protective shell or enclosure 16, that houses internal components including an x-ray radiation source 12 and a digital detector 20 that captures digital radiographic images of the subject 14, and also provides sufficient levels of radiation shielding to minimize or prevent x-rays emitted by the source 12 from exiting the enclosure 16. For volume imaging, source 12 and detector 20 are both moved into diametrically opposed positions, relative to imaging central axis 13, at different angular locations along the source/detector path 15 to acquire a number of 2-D projection images of the subject 14, each image acquired at one of the different angular locations. The acquired projection image data may then be stored in an electronic memory of the detector 20, transmitted by the detector 20 over a wide area network (WAN) 22 to a remote site 24 for processing, viewing, assessment, and storage of the image data. At remote site 24, a computer system or other processing system 30 may be in signal communication with the components of the imaging apparatus 40 to receive the digital images captured and transmitted by the detector 20 or the imaging apparatus 40. Computer system 30 may execute programs to reconstruct a digital volume image of the subject 14 using the received radiographic projection images. The digital volume image may be presented on a display 32 for viewing and assessment. The volume image may also be transmitted over the WAN 22 to other suitable networked computers (not shown) and to a digital image storage device located in database 26.

It may be appreciated that the embodiment shown in FIG. 1 allows imaging apparatus 40 to be easily transported to, and used at, a remote site for capturing and supplying projection images of a subject 14. A hospital or radiology practice may communicate over the WAN 22 and utilize satellite volume imaging stations comprising the imaging apparatus 40 that are remotely installed to provide a needed portable facility for obtaining patient image data, such as for screening or other procedures, without requiring the patient to travel to a central hospital or radiology facility. It should be noted that imaging apparatus 40 may also be used for tomosynthesis imaging, with appropriate modifications as described in more detail herein.

Figure 2A:
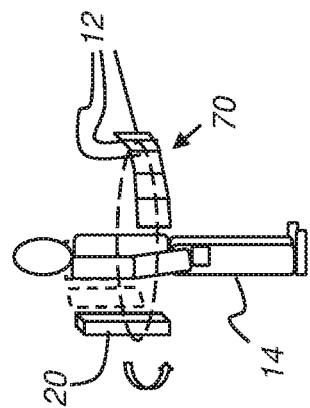
FIG. 2A is a schematic diagram of an exemplary scan pattern for acquiring projection images used for volume imaging.

To support the requirements of volume radiographic imaging, which utilizes multiple 2-D images, each taken at a different rotational angle about subject 14, and the programmed algorithms that reconstruct a 3-D image volume, CBCT imaging apparatus 40 may provide image capturing scanning movements in a number of ways. By way of example, FIG. 2A illustrates revolution of a radiographic energy source 12 and a digital detector 20 about a radial path 15, wherein the focal spot of the source 12 orbits the patient 14 while remaining in the plane of the radial path 15 at every image capture position in the scan. The orbital path of FIG. 2A may be most useful when the imaging region of interest of the subject 14 is positioned at or proximate the imaging central axis 13 (FIG. 1) of the radial path 15.

Figure 2B:
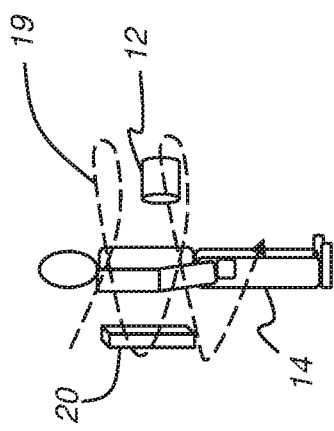
FIG. 2B is a schematic diagram of an exemplary scan pattern for acquiring projection images used for volume imaging.

FIG. 2B illustrates an alternate helical scan path 19 that may be used to generate a larger image volume. Other exemplary scan patterns that may be effective include reverse helical scan patterns that effect downward movement over one part of the scan and upward movement over another part of the scan, while the source and detector revolve about an imaging axis. Other scan patterns, including sinusoidal scanning, wherein the source and detector are continuously moving upward and downward parallel to an imaging axis while revolving about the imaging axis, may alternately be used. An elliptical scan may be of value, particularly for low-dose chest imaging, since an elliptical pattern may be compatible with the overall shape of the chest. It should also be noted that a partial revolution about the subject may be sufficient, depending on the amount of depth data that may be required for a particular case. Tomosynthesis imaging may also be provided with a stationary detector 20 and source 12 that is moved over an arc, for example, or with a stationary detector 20 and stationary source 12 and a moving patient 14. Tomosynthesis may also employ a linear scan, such as a scan wherein source 12 is moved vertically through a range of height positions, or along an arc less than 180° (FIGS. 3D-3E), while directing radiation energy through the subject 14 toward the detector 20.

Scanning movements as illustrated in FIGS. 2A and 2B, or other scan patterns, may be effected by any of a number of mechanisms, such as by revolving source 12 and detector 20 about a stationary subject 14. According to an alternate embodiment, scanning may be effected by rotating the patient while the source and detector remain stationary, such as by rotating a platform on which the patient is standing, for example.

Figure 2C:
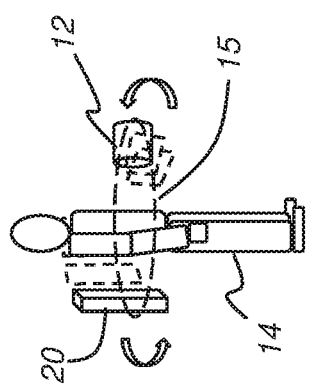
FIG. 2C is a schematic diagram that shows an exemplary scan pattern using an array of radiation sources.

According to an alternate embodiment of the present disclosure, as shown schematically in FIG. 2C, an array 70 of multiple x-ray sources 12 arranged in an arc may be provided for obtaining projection images. For CT or CBCT imaging, the individual sources 12 may be energized in a timed sequence, corresponding with a complementary movement of detector 20 about the subject 14. In one tomosynthesis imaging embodiment, detector 20 may be stationary as a plurality of sources 12 is energized in a timed programmed sequence. The sources 12 in array 70 may include distributed carbon nanotube (CNT) emissive devices, for example, configured to be individually energized, or fired, for providing x-ray radiation in a predetermined timed sequence.

Figure 3C:
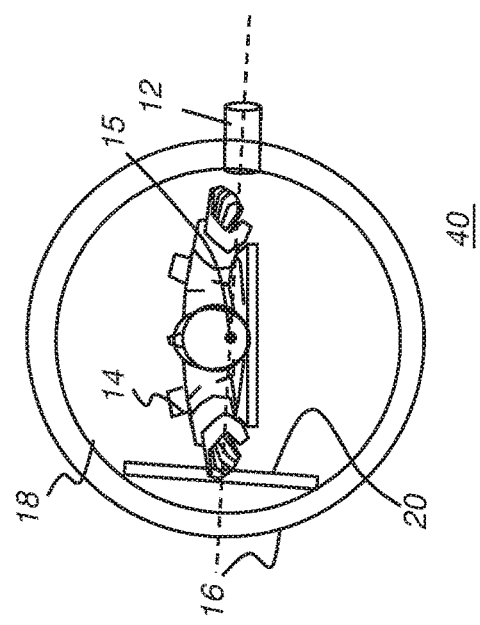
FIGS. 3A, 3B, and 3C are top views of an exemplary imaging system embodiment that shows a cone-beam computed tomography (CBCT) imaging apparatus wherein the source and detector orbit the subject for serial projection image acquisition.
Figure 3B:
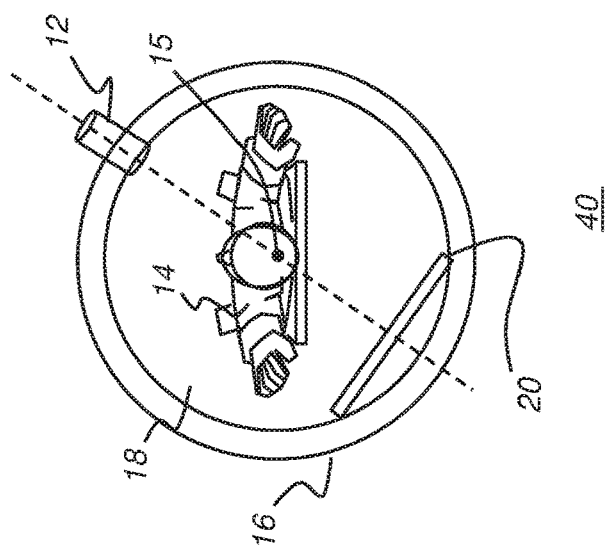
Figure 3A:
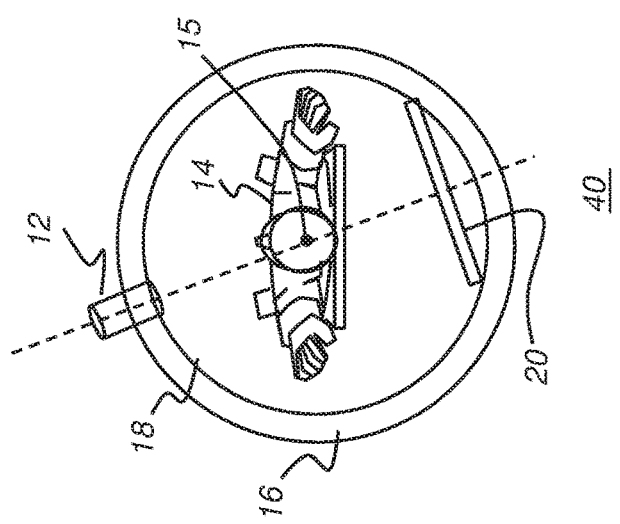

Relative rotation between the subject 14 and the radiation imaging components may be provided in any of a number of ways. FIGS. 3A, 3B, and 3C show, from a top view, scanner movement for an embodiment in which the subject 14 is standing in a stationary position while source 12 and detector 20 revolve about a central axis 15 at or near the patient's position. Subject 14 may be standing on a stationary platform 18 while source 12 and detector 20 are attached to a cylindrical shell or enclosure 16 that rotates about the patient 14 positioned at or near the central axis 15 while platform 18 remains still. The source and detector travel paths may be defined using one or more rigid tracks that guide the paths of source 12 and detector 20 within the enclosure as an imaging session proceeds. The use of tracks or other guidance may help to provide an elliptical scan pattern or other suitable scan trajectory, for example.

Figure 3E:
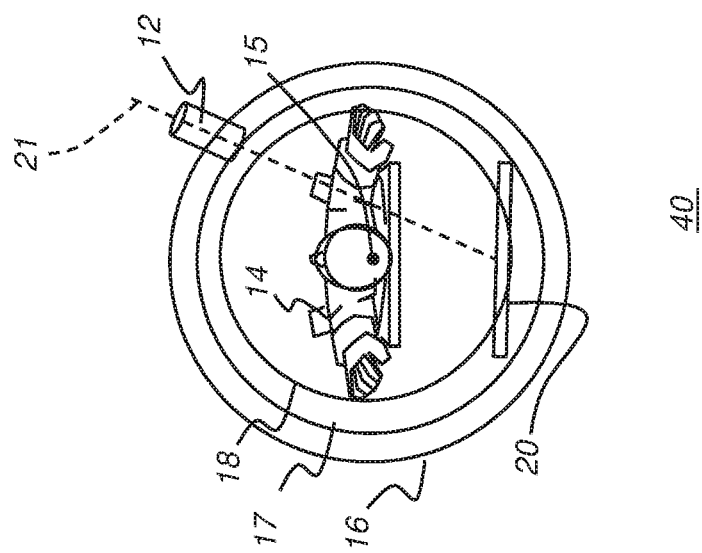
FIGS. 3D and 3E are top views of an exemplary imaging system showing an imaging apparatus with the source moving along an arc and the detector remaining stationary for tomosynthesis imaging.
Figure 3D:
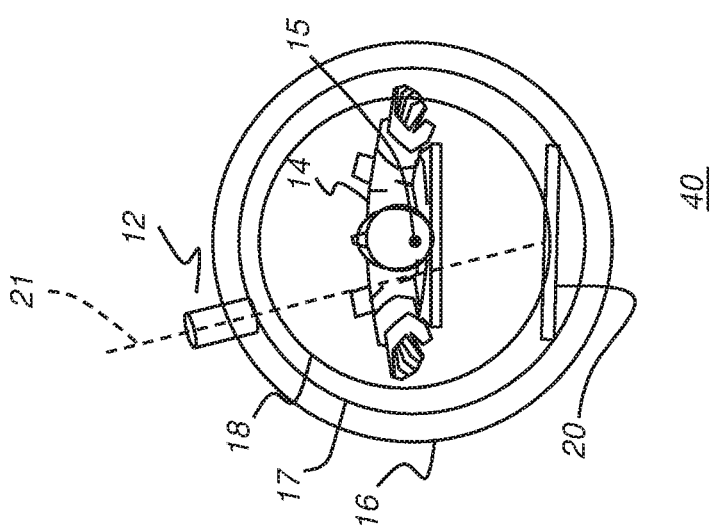

In one embodiment, both CBCT and tomosynthesis imaging may be performed using one imaging apparatus 40. One mechanism may be used to revolve source 12 about the patient who is positioned at or near the central axis 15, while a separate mechanism may be used to revolve the detector 20. For CBCT operation, the two mechanisms are linked so that source 12 and detector 20 both simultaneously and synchronously revolve about the subject 14 positioned at or near at central axis 15. In the embodiment shown in FIGS. 3D and 3E, a tomosynthesis imaging mechanism may include separable assemblies allowing the detector 20 to be fixed in position so that only source 12 moves along an arc of revolution about central axis 15, as shown. In the embodiment of FIGS. 3D and 3E, source 12 may be coupled to rotatable gantry 17 and detector 20 may be coupled to a stationary shell 16. Source 12 itself may be rotated during its revolving movement around central axis 15 so that it is aimed at the detector 20 such that a central ray 21 emitted by the source 12 is directed substantially toward a center of detector 20. It can readily be appreciated that a number of different mechanical arrangements may be used for coupled or de-coupled orbital movement of source 12 and detector 20 about the patient.

Figure 4C:
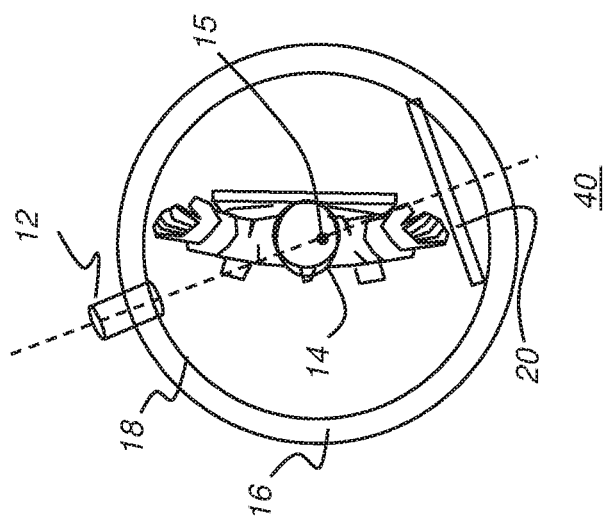
FIGS. 4A, 4B, and 4C are top views that show an exemplary CBCT imaging apparatus wherein the subject is rotated between the source and detector for image acquisition.
Figure 4B:
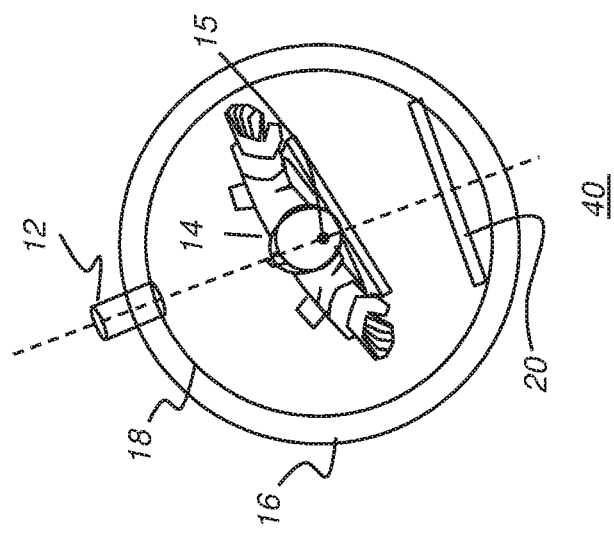
Figure 4A:
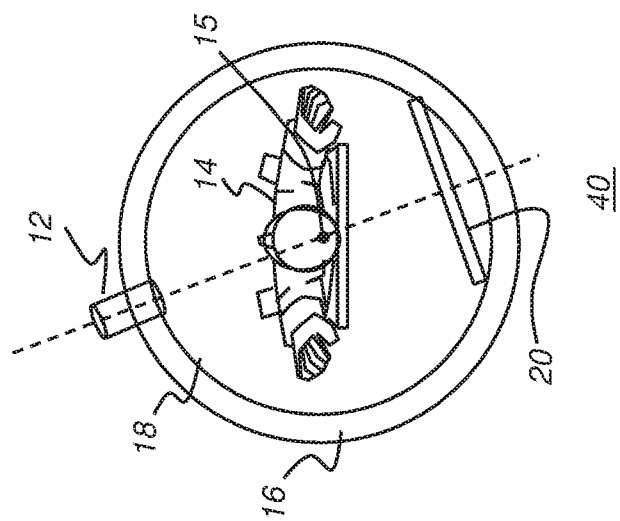

FIGS. 4A, 4B, and 4C show top views of a scanning procedure using imaging apparatus 40 in an embodiment in which the standing subject 14 rotates while maintaining at least a portion of the subject's body, such as a torso, proximate to or at the central imaging axis 15, while source 12 and detector 20 remain stationary. Subject 14 is standing on a rotating platform 18 while source 12 and detector 20 are attached to a cylindrical enclosure 16 that remains in a stationary position. Belts, straps, and/or a support attached to the platform 18 and extending upward to support the patient 14, and/or other supporting features may be provided to secure the patient 14 in a position oriented for optimal radiographic imaging within the enclosure 16. Additional support features may include a headrest secured in an appropriate position to support the head of the patient 14, and/or hand grips to assure that the patient's hands and arms are appropriately positioned.

The imaging apparatus 40 may include a voltage supply (not shown) electrically connected to the x-ray source to provide adjustable x-ray energy levels. Chest imaging, for example, may require increased x-ray energy for obtaining images of the patient from a lateral view, since there may be more patient mass between the source and detector in that direction; and less energy could be used for the posterior-anterior (PA) image. X-ray energy levels may be accordingly varied at different imaging positions during the scan. A plurality of detectors 20 having different sizes and relative dimensions may be provided to address the particular requirements of the imaging apparatus 40 and the patient. For example, a detector 20 width may be selected to be larger than the width of the patient's lungs. Detector 20 height may be selected relative to average lung size for a local patient population.

FIGS. 5A, 5B, 6, and 7 show lateral views of the patient 14 within an enclosure 16 provided by imaging apparatus 40. Various components and configurations are illustrated for positioning and supporting the patient 14 within the enclosure 16 during the scanning procedure. Considerations for patient positioning include positioning the patient's arms up and away from the chest area during scanning. As illustrated in FIGS. 5A and 5B, handles or a handle bar 42 or other device may be attached to the shell 16 for grasping by the patient.

An adjustable platform, or backrest, 46 may be attached to the imaging apparatus 40 to provide support for the patient 14 while the patient 14 leans against it and may be particularly useful where obtaining images of the patient 14 may require that the patient not be positioned in a vertical orientation. Backrest 46 may be adjustable for angle, such as by including an adjustable support member 34, and for patient height. Backrest 46 can support the person during image capture and may be vertical or obliquely disposed at an angle away from vertical, such as an angle between about 5 degrees and about 15 degrees away from a vertical position, for example. Patient support components that work with backrest 46 may include handle bar 42 devices, straps that extend around a torso of patient 14, suction devices, releasable fasteners such as hook-and-loop fasteners, or other mechanisms for temporarily securing the patient in position and for holding the patient's arms comfortably in place, either in an upward position, away from the chest, as shown in FIGS. 5A-5B or in other suitable positions. The backrest 46 support may be positioned vertically or at a slight slant angle when the enclosure shell 16 is unoccupied, and may be designed to tilt the patient into a suitable position for imaging while the patient is leaning against it.

Figure 6:
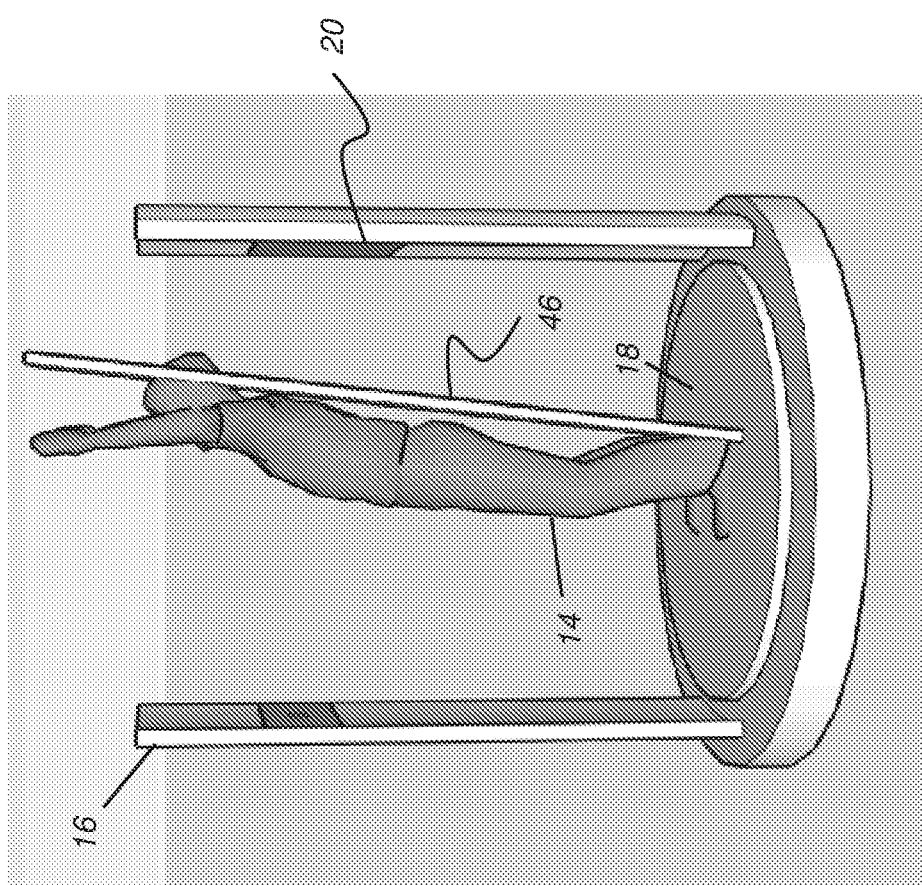
FIG. 6 is a perspective view that shows a patient leaning against an exemplary patient support component with a tilted backrest within an enclosure chamber used for CBCT image acquisition.
Figure 7:
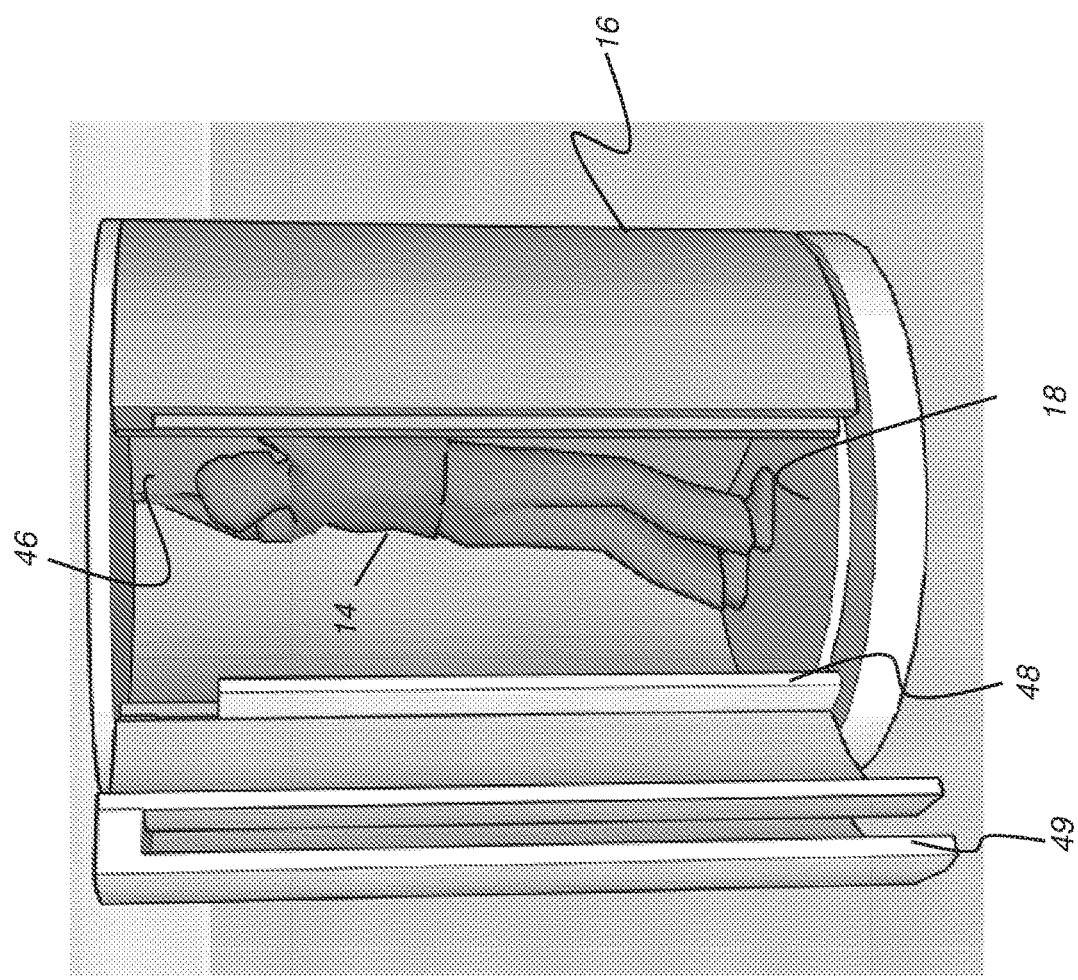
FIG. 7 is a perspective view showing the subject patient leaning against an exemplary supporting member within an enclosure chamber used for CBCT image acquisition.

FIG. 6 shows the subject 14 in a non-vertical position but leaning backward against backrest 46, obliquely disposed in a tilted position within imaging apparatus 40. FIG. 7 shows an alternate embodiment with subject 14 leaning forward against backrest 46. In this configuration, the subject 14 also has arms raised above the chest area. FIG. 7 also shows a configuration that uses a radiopaque sliding door 48 that may be closed to provide shielding during the imaging session as well as a rotatable door 49. In addition to patient 14 support and stabilization, there are a number of other features that may be provided for x-ray shielding and enclosure. The extent of the shielding above and below the patient depends, in part, on measured exposure levels. In an alternate embodiment, the enclosure 16 may include a variable height that may be changed based on factors such as the examination type and patient height, for example.

Where the enclosure fully encloses the subject 14 during imaging, one or more windows may be provided to allow light to enter the enclosure from the surrounding environment and, optionally, visibility of the surrounding environment for the enclosed patient. According to one embodiment shown in FIG. 8, a leaded glass window 92 may be provided along the top of the enclosure, with one or more additional windows (not shown) provided in lower portions of the enclosure. The material used for windows may be radiopaque, in order to block radiographic energy, but is transparent to visible light. This may provide a more comfortable and less confining environment for the subject 14 being imaged.

Figure 8:
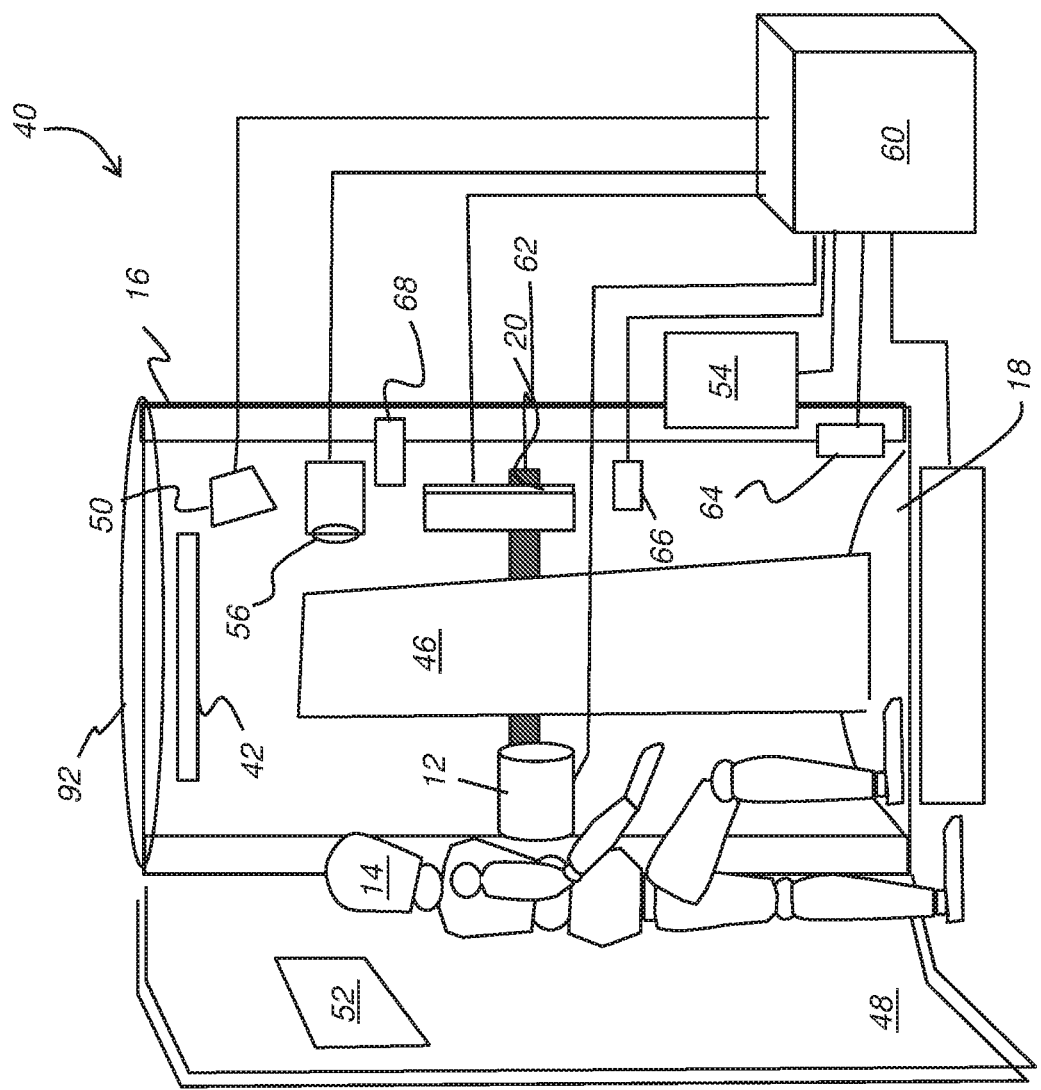
FIG. 8 is a schematic diagram showing a number of exemplary control components for image acquisition using an enclosure imaging shell of one embodiment of the present disclosure.

FIG. 8 is a schematic diagram that shows control features and supporting components that allow CBCT imaging apparatus 40 to be used in clinical applications and at sites that do not have a trained technician to assist in setting up and running the imaging exam. As part of imaging apparatus 40 a controller 60, which may include a programmable processor, provides control functions and monitoring of apparatus operation and also provides the needed WAN interface for communication of control signals and transfer of acquired image data.

Patient access to the imaging area inside enclosure 16 may be provided via a sliding or hinged door 48, which may be lockable using a locking mechanism controlled by an access controller 54. Digital access control may be provided by a number of mechanisms. For example, access controller 54 may be programmed to unlock the locking mechanism for the door 48 in response to receiving an access code that is read from an encoded token or encoded ID card containing an authorized digital access code as a type of electronic identification, which token or ID card may be provided to the patient data by a doctor or by a medical facility. A reader 68 may be connected to access controller 54 which reader 68 may include a magnetic reader for detecting magnetically detectable digital access data, such as provided on a magnetic strip on an ID card, for entry and use of the imaging apparatus 40; a laser reader for detecting 1D or 2D bar codes; other biomarker detectors such as fingerprint readers; as well as audio detectors; an optical reader for reading optically detectable access data; or a combination thereof.

Access controller 54 may be electrically connected to a digital camera 56 that is configured to detect and verify patient ID using iris scanning or facial recognition, for example, to capture and record patient identification or exam documentation, or a combination thereof. Alternately, for digital access control, the patient 14 may be provided with a code for keypad entry in order to use the imaging apparatus 40. Using such identification features may allow imaging apparatus 40 to be installed at an unattended site, such as in a public area, shopping mall, or other public or private facility for use only by authorized patients. An interlock apparatus 64 may be provided, including both hardware and software components and sensors for preventing operation where door 48 is not properly closed or the patient is not detected in a correct position for the required imaging procedure.

A speaker 50 may be provided within the enclosure 16 in order to provide digitally prerecorded or live audio instructional messages to the patient immediately prior to and during an imaging procedure. These may include messages automatically responsive to sensors within the enclosure 16 detecting a proper or improper position of the patient 14 within the imaging apparatus 40 before and during execution of the imaging procedure. The speaker 50 may also be used to play music, such as might be useful for assisting relaxation. A display monitor 52 may be provided within the enclosure 16 for displaying instructional text and videos, which text and videos may correspond in time to the audio messages described herein. The monitor 52 may also be used to display still and moving images to complement the playback of relaxation music.

In one embodiment, the camera 56 may be used to detect a height of the subject 14 and transmit detected height data to controller 60, wherein the controller 60, in turn, may signal a mechanism to adjust a height of the radial travel path 15 (FIG. 2A) above the platform 18, for the source 12 and detector 20. A WAN-connected microphone 66, video camera 56, and speaker 50 may be provided to allow patient 14 to communicate with remote personnel in the event that live audio and/or video network streaming instruction and response is desired.

Controller 60 may also be electrically connected to a motorized mechanism for controlling movement of a transport apparatus 62 that provides the orbital movement to x-ray source 12 and detector 20 for x-ray scanning. Additional actuators of transport apparatus 62 may also be provided to change a height of the radial scan path 15, helical pitch for a helical scan path 19, and other variables related to the scan procedure.

Enclosure 16 may be formed from any of a number of materials that provide a sufficient measure of absorption of x-ray radiation to meet regulatory requirements. Enclosure 16 may be formed from lead or other radiopaque material. Alternately, enclosure 16 may be covered or coated with a radiopaque material. External and internal dimensions of enclosure 16 should allow for sufficient shielding of the standing patient and proper spacing of patient 14, and source 12 and detector 20 assembly components. In one embodiment, a circular enclosure 16 may include an interior diameter configured to be between about 28 inches and 38 inches, which may result in providing a usable floor or platform 18 area between about 600 square inches and 1200 square inches. In one embodiment, a height of enclosure 16 extends from about 4 feet to about 9 feet, allowing configurations that enclose only a part of the patient 14 anatomy within the enclosure 16 or the entirety of patient 14. In one such embodiment, the interior volume of enclosure 16 may range between about 17 cubic feet and about 71 cubic feet. The interior volume allows patient movement therein such as for assuming a proper imaging position, and otherwise adjusting body position for radiographic imaging. Thus, the size of imaging apparatus 40 is consistent with embodiments thereof that are portable or transportable easily to locations remote from large centralized medical imaging facilities.

Figure 9:
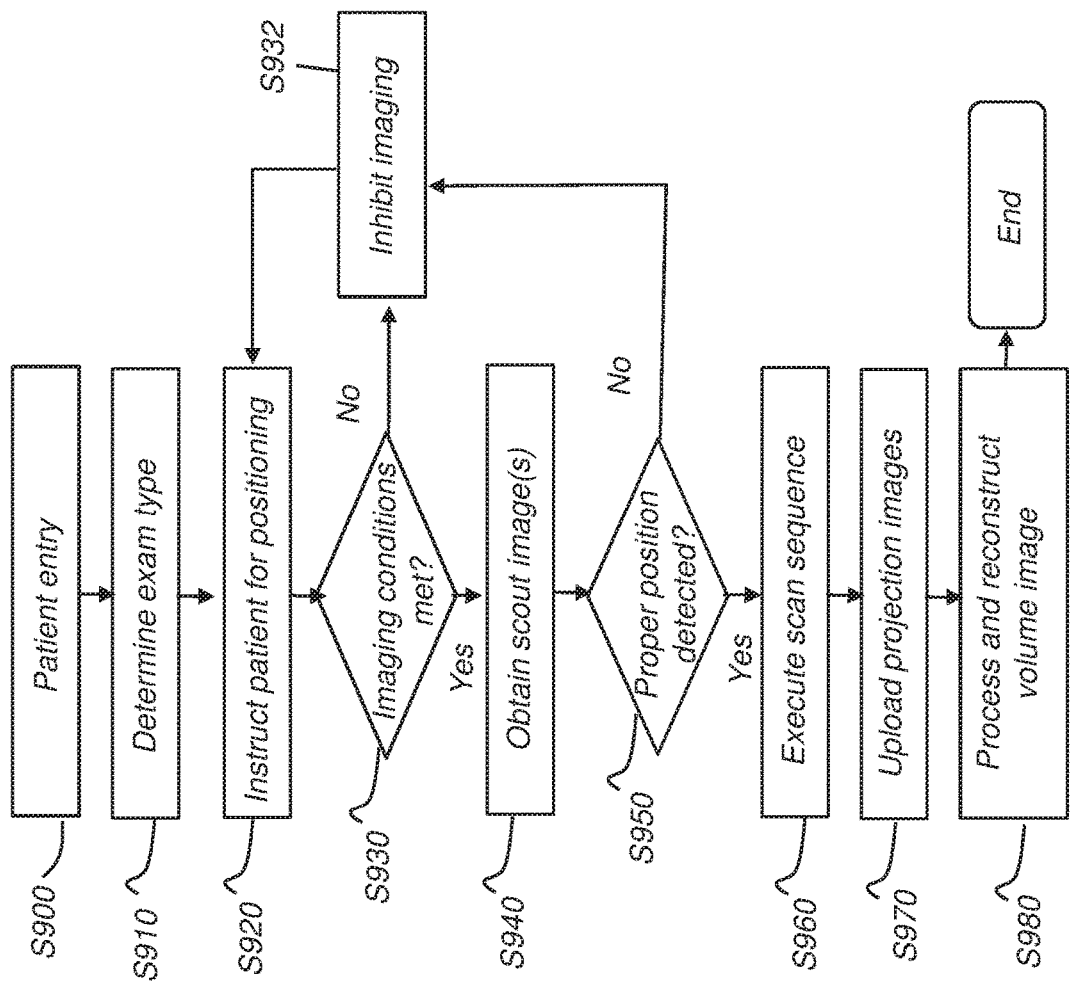
FIG. 9 is a logic flow diagram that shows an exemplary sequence for automatically obtaining multiple 2-D radiographic images of a subject without technician assistance according to an embodiment of the present disclosure.

With respect to the logic flow diagram of FIG. 9, a method is disclosed for automatically obtaining multiple 2-D radiographic images of a subject using imaging apparatus 40 without requiring on-site personal technician assistance according to an embodiment of the present disclosure. In a patient access step S900, the patient 14 is permitted to enter the imaging apparatus 40. An electronically controlled lock connected to the controller 60 releases the door to be opened upon receiving an unlock command from controller 60, thereby allowing the patient to open the door 48 and enter the imaging apparatus 40 alone after a proper access ID procedure is followed. A proper access procedure for allowing patient access into enclosure 16 may be accomplished in any of a number of ways, such as by providing the patient with an encoded ID card, or ID token from a doctor or medical facility, which is detected and recognized by a reading apparatus 68 electrically connected to the imaging apparatus 40. An identification card or other permission document may alternately be used or may be required to verify patient identity.

In an exam determination step S910, the controller 60, electrically connected to the imaging apparatus 40 and to a WAN 22 determines the type of exam prescribed for the identified patient 14. This may have been provided on access documentation carried by the patient and communicated to the imaging apparatus 40, or it may be accessed and downloaded from WAN connected database 26, for example, by automatically communicating the recognized patient ID to the database 26 which uses the ID as an index into the database 26 to retrieve and return the prescribed exam type. In a patient instruction step S920, the patient 14 may be provided with instructions for proper positioning to allow the image acquisition procedure. This may include pre-recorded audio played back over the speaker 50, text messages displayed on a monitor 52, or recorded video instructions played back using both the speaker 50 and monitor 52, or even live streamed video via the connected WAN 22 from a technician or practitioner who may communicate with and view the patient 14 over the same two-way video stream using the camera 56 within imaging apparatus 40. Audio and/or visual feedback may be provided to the patient 14 to indicate successful positioning and equipment setup.

An imaging verification step S930 then executes, in which the imaging apparatus and/or the remote technician checks that the required imaging conditions are met. These may include hardware conditions such as, for example, proper closing of doors 48, 49 for radiation shielding, etc. If the imaging conditions are not met at step S930, imaging is inhibited at step S932 and the method returns to step S920 for additional patient instruction as described above. If the imaging conditions are met at step S930, a scout image acquisition step S940 may be performed to obtain and analyze at least one low-dose scout image of patient 14 as a prelude to subsequent volume imaging activity. The scout image allows a quick check of calibration, equipment settings, and patient position, to verify that equipment and patient setup are acceptable. The scout image may also be used to verify that power levels are acceptable for subsequent imaging. For some imaging cases, a two-view scout image may be obtained, such as one lateral view and one PA view.

A position detecting step S950 is then executed, in which the imaging apparatus checks for proper patient positioning for the selected examination. In addition to using image results from the scout image, this step may use recorded information from camera 56, live video information transmitted from camera 56 to a remote technician, and information from one or more sensors that are in signal communication with controller 60. A laser source and detector, for example, may be placed within enclosure 16 to verify the position of patient 14. If patient positioning conditions are unsatisfactory at step S950, an inhibit step S932 prevents imaging from proceeding, and the method returns to step S920 to activate additional instructions as described herein, additional review of proper setup and patient positioning procedures, and to communicate any other additional audio and/or visual instructions.

If proper positioning is verified at step S950, a scan step S960 is then performed according to a programmed imaging sequence associated with the required exam type. For example, the scan step may include moving and activating the (source and detector) imaging components and acquiring 2-D projection images for the associated exam type. An image upload step S970 then uploads the acquired projection images to a central processor 30 (FIG. 1) over WAN 22, or other suitable location. A processing and reconstruction step S980 is then executed at the central processor 30 for reconstructing the volume image using an appropriate 3-D reconstruction algorithm. The reconstructed image may be transmitted to a local or network connected facility for viewing by medical personnel, or the reconstructed image may be stored for later transmission and/or viewing as part of processing step S980.

Alternative embodiments consistent with the disclosure hereinabove may include an apparatus for imaging a subject, wherein the apparatus comprises a plurality of x-ray sources, such as carbon nanotube sources, in an x-ray assembly that are electrically connected to be controllably individually fired. An x-ray detector may be positioned to capture radiographic images of a patient positioned between the source and detector. A controller may be configured to selectively fire two or more of the sources in a predetermined sequence and a predetermined timing, wherein the plurality of sources and the detector are configured to capture and store a plurality of radiographic images of the subject while sequentially firing the sources. A transport mechanism may be provided to move the detector, with respect to a standing subject, to respective positions corresponding to the positions of each of the plurality of x-ray sources. A portable x-ray shielded enclosure surrounds the source, the detector, the transport mechanism, and the subject to be imaged.

In another alternative embodiment, a method for acquiring a volume image of a subject includes unlocking an entry to an imaging enclosure in response to receiving an access code associated with the subject. Corresponding hardware assemblies within the enclosure automatically provide audio and visual instructions to the subject for positioning himself or herself within the imaging enclosure. Corresponding visual cues or indicators may be provided on interior surfaces of the enclosure, such as floors, walls, and ceilings. Handles and other body supports may be provided to support the subject in a correct orientation with respect to imaging components such as an x-ray source and detector. After verifying correct positioning, a scout image may be obtained to further verify correct subject positioning for a predetermined exam type to be performed. The subject may be radiographically imaged from a plurality of source and/or detector positions, and the captured images of the subject may be uploaded. The uploaded projection images may be processed in the usual course, such as reconstructing a volume image based on the uploaded images. Any, or both, of the captured and reconstructed images may be displayed, stored, or otherwise transmitted to remote computer systems.

In another alternative embodiment, an apparatus for obtaining a sequence of radiographic images of a subject includes a portable radiation shielded enclosure having sufficient interior room to surround a subject to be imaged between an x-ray source and an x-ray detector. The source and detector may be configured to acquire a plurality of radiographic images of the subject at different angles. A patient support may be provided to support the subject in a suitable position on a platform within the enclosure for image acquisition. A motor controlled mechanism incrementally moves the source or both the source and detector for repeated image acquisition at different angles. The plurality of images so obtained may include a radial scan, or a helical scan, for example.

For exemplary functions described herein and/or performed as described with reference to the figures, the system processor, host computer or the radiographic imaging system/unit may be implemented, for example, but not limited to using one or more of a conventional general purpose processor, digital computer, microprocessor, microcontroller, RISC (reduced instruction set computer) processor, CISC (complex instruction set computer) processor, SIMD (single instruction multiple data) processor, signal processor, CPU (central processing unit), ALU (arithmetic logic unit), GPU (graphics processing unit), VDSP (video digital signal processor) and/or similar computational machines, programmed according to the teachings of the present specification, as will be apparent to those skilled in the relevant art(s). Appropriate software, firmware, coding, routines, instructions, opcodes, microcode, and/or program modules may readily be prepared by skilled programmers based on the teachings of the present disclosure, as will also be apparent to those skilled in the relevant art(s). The software may be generally executed from a medium or several media by one or more of the processors of the machine implementation.

Consistent with one embodiment, the present invention utilizes a computer program with stored instructions that control system functions for image acquisition and image data processing for image data that may be stored and accessed from an electronic memory. As may be appreciated by those skilled in the image processing arts, a computer program of an embodiment of the present invention may be utilized by a suitable, general-purpose computer system, such as a personal computer or workstation that acts as an image processor. However, many other types of computer systems may be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that may be connected to the image processor by way of the internet or other network or communication medium. Those skilled in the art will further readily recognize that the equivalent of such a computer program product may also be constructed in hardware.

It is noted that the term "memory", equivalent to "computer-accessible memory" in the context of the present disclosure, may refer to any type of temporary or more enduring data storage workspace used for storing and operating upon image data and accessible to a computer system, including a database. The memory could be non-volatile, using, for example, a long-term storage medium such as magnetic or optical storage. Alternately, the memory could be of a more volatile nature, using an electronic circuit, such as random-access memory (RAM) that may be used as a temporary buffer or workspace by a microprocessor or other control logic processor device. Display data, for example, is typically stored in a temporary storage buffer that may be directly associated with a display device and may be periodically refreshed as needed in order to provide displayed data. This temporary storage buffer may also be considered to be a memory, as the term may be used in the present disclosure. Memory may be also used as the data workspace for executing and storing intermediate and final results of calculations and other processing. Computer-accessible memory may be volatile, non-volatile, or a hybrid combination of volatile and non-volatile types.

It is understood that the computer program product of the present invention may make use of various image manipulation algorithms and processes that are well known. It will be further understood that the computer program product embodiment of the present invention may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that may contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that may direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An apparatus comprising:
   an x-ray source assembly configured to revolve about a central axis;
   an x-ray detector assembly configured to revolve about the central axis to capture and store a plurality of radiographic images of a portion of a patient positioned at or near the central axis;
   sensors to detect a position of the patient at or near the central axis;
   a network connected microphone, monitor, video camera and speaker each selectively activatable to allow audio/visual communication over the network between the patient and remote personnel; and
   an x-ray shielded enclosure attached to the x-ray source assembly and the x-ray detector assembly, the x-ray shielded enclosure configured to entirely enclose the source assembly, the detector assembly and the patient, wherein the apparatus is configured to be transportable as a unit.

2. The apparatus of claim 1, wherein the source assembly and the detector assembly are configured to revolve along a radial path or a helical path relative to the patient positioned at or near the central axis.

3. The apparatus of claim 1, wherein the x-ray shielded enclosure comprises a cylindrical shape having an interior diameter between about 28 inches and about 38 inches and a height of about 9 feet.

4. The apparatus of claim 1, wherein the enclosure comprises an electronically controlled lock configured to unlock only in response to receiving a digital access code.

5. The apparatus of claim 4, wherein the enclosure comprises a door to allow entry into, and exit out of, the enclosure, the door configured to be locked and unlocked by the electronically controlled lock.

6. The apparatus of claim 4, wherein the enclosure further comprises transducer circuitry to convert magnetic signals, reflected laser signals, iris scanned signals, biomarker signals, audio signals, or optical signals into the digital access code.

7. The apparatus of claim 4, wherein the enclosure further comprises a reader to identify an encoded digital access code on an ID card or token.

8. The apparatus of claim 1, further comprising a support within the enclosure to support the patient at an angle of between about 5 degrees and about 15 degrees away from a vertical position.

9. The apparatus of claim 1, wherein the sensors comprise a laser source and a laser detector configured to detect a position of the patient at or near the central axis.

10. The apparatus of claim 1, wherein the speaker is configured to output live or electronically recorded audio instructions.

11. The apparatus of claim 1, wherein the x-ray detector assembly is configured to revolve about the central axis simultaneously with the x-ray source assembly.

12. The apparatus of claim 1, further comprising a height adjustable overhead apparatus configured to retain the patient's arms in an extended position while capturing radiographic images of the patient.

13. The apparatus of claim 12, wherein the height adjustable overhead apparatus comprises handles configured to be grasped by the patient.

14. The apparatus of claim 1, wherein the enclosure comprises a window fabricated from a radiopaque material transparent to visible light.

15. The apparatus of claim 1, further comprising an x-ray assembly controller, wherein the x-ray source comprises an array of x-ray sources configured to be independently energized, and wherein the controller is configured to selectively energize two or more of the x-ray sources in a predetermined sequence and a predetermined timing.

16. The apparatus of claim 1, further comprising a platform for the patient to stand on, the platform having an area of between about 600 square inches and about 1200 square inches.

17. The apparatus of claim 1, further comprising an interior volume to allow movement of the patient therein of between about 17 cubic feet and about 71 cubic feet.

18. An apparatus comprising:
a stationary x-ray shielded cylindrical enclosure having a central axis;
an x-ray source assembly positioned on one side of the central axis and attached to the cylindrical enclosure;
an x-ray detector assembly positioned on a second side of the central axis opposite the x-ray source assembly and attached to the cylindrical enclosure, the x-ray detector assembly configured to capture and store a plurality of radiographic images of a patient standing at or near the central axis; and
a circular platform within the cylindrical enclosure, the platform configured to support the patient standing thereon and to rotate the standing patient between the source assembly and the detector assembly, wherein the source assembly and the detector assembly are configured to capture and store a plurality of radiographic images of the patient; and
the stationary x-ray shielded cylindrical enclosure configured to completely enclose the source assembly, the detector assembly, the platform and the standing patient, wherein the apparatus is configured to be transportable as a unit.

19. The apparatus of claim 18, wherein the cylindrical enclosure comprises an interior diameter between about 28 inches and 38 inches and a height of about 9 feet.

20. An apparatus comprising:
an x-ray detector, the x-ray detector fixed in a stationary position;
an x-ray source, the x-ray source configured to rotate while translating between two terminal positions about a patient in order to emit x-rays toward the patient and the x-ray detector at predetermined times while translating between the two terminal positions;
sensors to detect a position of the patient;
a network connected microphone, monitor, video camera and speaker each selectively activatable to allow audio/visual communication over the network between the patient and remote personnel to assist in proper positioning of the patient; and
a cylindrical x-ray shielded enclosure comprising an interior diameter between about 28 inches and 38 inches and a height of about 9 feet, the x-ray shielded enclosure attached to the x-ray source and the x-ray detector, the x-ray shielded enclosure configured to entirely enclose the x-ray source, the x-ray detector, the sensors and the patient,
wherein the apparatus is configured to be transportable as a unitary integrated whole, and wherein the x-ray detector is configured to capture radiographic images of the patient standing between the x-ray source and the x-ray detector.

* * * * *